United States Patent [19]

Kurtz et al.

[11] Patent Number: 4,469,484

[45] Date of Patent: Sep. 4, 1984

[54] SURGICAL DRAINAGE DEVICE WITH AUTOMATIC NEGATIVE PRESSURE RELIEF SYSTEM

[75] Inventors: Robert J. Kurtz, New York; Joseph M. LiCausi, Port Jefferson Station, both of N.Y.

[73] Assignee: Bio Research Inc., Farmingdale, N.Y.

[21] Appl. No.: 386,435

[22] Filed: Jun. 8, 1982

[51] Int. Cl.³ .............................................. A61M 1/00
[52] U.S. Cl. ..................................... 604/321; 137/205
[58] Field of Search ................ 137/205; 604/317–321; 141/48, 67

[56] References Cited

U.S. PATENT DOCUMENTS

| | | | |
|---|---|---|---|
| 3,683,913 | 8/1972 | Kurtz et al. | 128/276 |
| 3,861,390 | 1/1975 | Schachet | 604/321 |
| 3,924,624 | 12/1975 | Schachet | 604/321 |
| 4,195,633 | 4/1980 | Nehring et al. | 604/318 |

Primary Examiner—C. Fred Rosenbaum
Assistant Examiner—J. L. Kruter
Attorney, Agent, or Firm—Larson and Taylor

[57] ABSTRACT

A surgical underwater drainage device for draining fluids from the body of a patient which is provided with an automatic negative pressure relief system is disclosed. The underwater drainage device includes a collection chamber, an underwater seal chamber and/or its equivalent, and a suction control chamber. In one embodiment a negative pressure relief valve is normally closed and provides a bypass around the liquid seal and/or its equivalent of the underwater seal chamber. When excess negativity occurs in the collection chamber and/or the thoracotomy tube, the relief valve opens automatically to slowly relieve the excess negativity. The relief valve also prevents flow to the collection chamber and/or the thoracotomy tube when the pressure in the collection chamber is equal to or greater than a predetermined minimum below the pressure on the opposite side of the seal of the underwater seal chamber or its equivalent. In another embodiment of the invention, a small bore tube is connected between the suction control chamber. The bore of the tube provides an open passageway between the two chambers but it tends to equalize the degree of negativity in the two chambers over a period of time. Thus, excess negativity within the thoracotomy tube will be slowly relieved.

6 Claims, 2 Drawing Figures

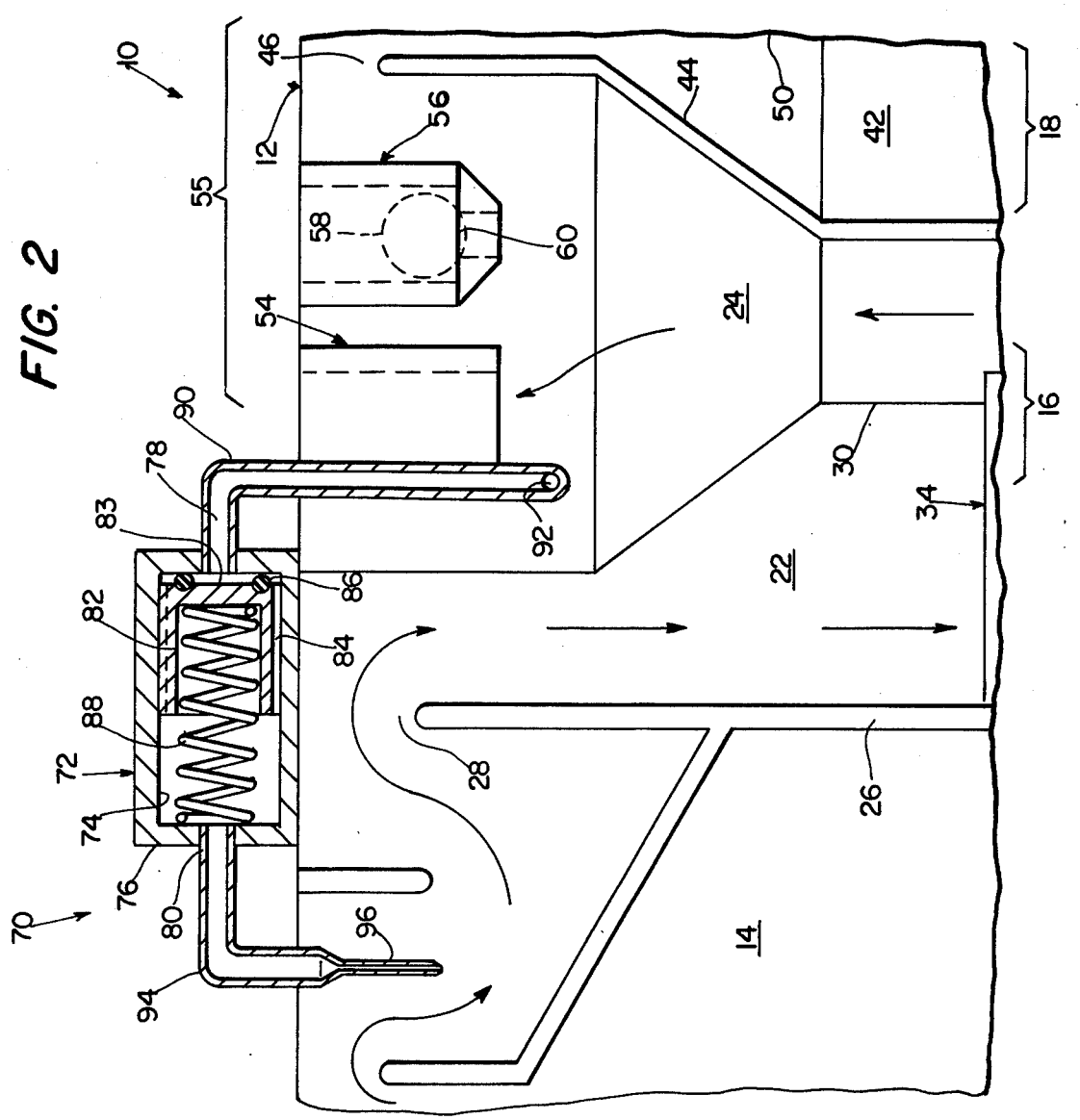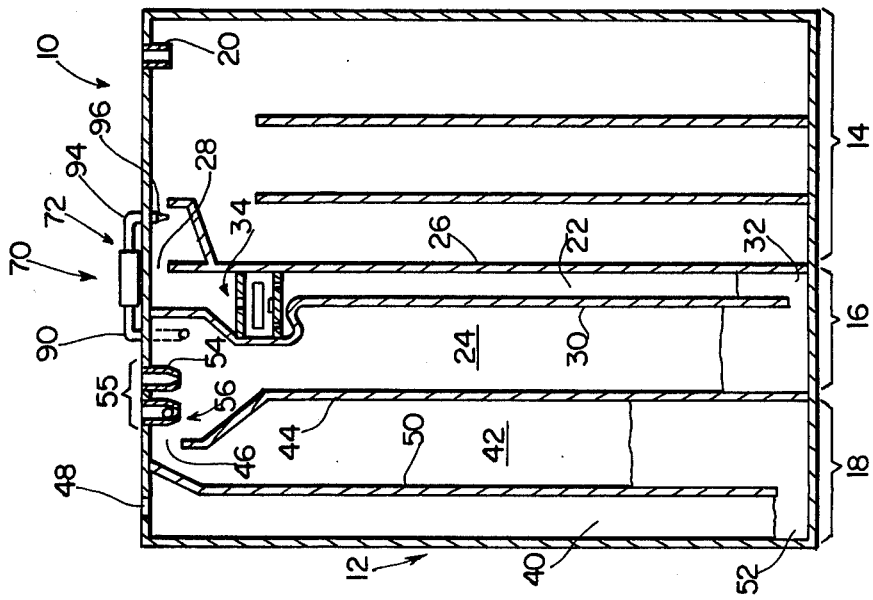

SURGICAL DRAINAGE DEVICE WITH AUTOMATIC NEGATIVE PRESSURE RELIEF SYSTEM

FIELD OF THE INVENTION

This invention relates to a surgical underwater drainage system used in draining fluids from the body, e.g. the pleural cavity, and is particularly concerned with an improved drainage system by which excess negativity within the body cavity is safely and automatically relieved.

BACKGROUND OF THE INVENTION

It is essential for normal breathing that the space within the pleural cavity surrounding the lungs be free of liquid and be subject to a negative pressure so as to draw the lungs outwardly to fill this pleural cavity in order to permit proper breathing. Any invasion of the pleural cavity such as caused by lung surgery or foreign objects which pierce the rib cage or such as occur, for example, where the patient has pleurisy, generates fluids in the pleural cavity which tend to obstruct normal breathing. It is necessary to provide a device which can remove these fluids from the pleural cavity and at the same time ensure that the desired degree of negative pressure imposed by the suction control chamber is approximately maintained within the pleural cavity.

Two of the basic types of apparatus which have been used for this purpose are shown, for example, in U.S. Pat. Nos. 3,363,626 and 3,363,627, and in pending U.S. Application Ser. No. 120,295 filed Feb. 11, 1980, now U.S. Pat. No. 4,324,244 issued Apr. 13, 1982 which are herein incorporated by reference. The first of these apparatuses provides three chambers, one chamber comprising a collection chamber for collecting the fluids drained from the pleural cavity through a thoracotomy tube, a second chamber known as an underwater seal chamber which protects the pleural cavity from being subject to atmospheric pressure, and a third chamber known as a suction control chamber which serves to regulate the degree of negative pressure within the pleural cavity. The other of these apparatuses provides a collection chamber with an underwater seal chamber located at the upper end thereof adjacent the lower end of the thoracotomy tube. Secretions from the body cavity form the underwater seal and excess secretions thereafter overflow into the collection chamber. These types of apparatuses have been highly successful in both removing fluids from the pleural cavity and in maintaining the desired degree of negativity within the pleural cavity.

It has been found that doctors frequently will "milk" the thoracotomy tubes in an effort to remove any clots or obstructions from the tube. This milking of the tube is achieved by squeezing the flexible thoracotomy tube adjacent the upper end and drawing the fingers down the tube to cause the fluids within the tube to be passed out the lower end of the tube and into the collection chamber. Obviously, this action has the effect of substantially lowering the degree of negativity within the pleural cavity. Such high negativity can be damaging to the pleural cavity and may also cause the liquid within a combined water seal-collection chamber to be drawn up into the pleural cavity. In addition, the entire water seal can be lost into the pleural space or the collection chamber during periods of high negativity in the pleural cavity. The loss of the water seal has the potential for causing pneumothorax in the event that the suction becomes disconnected. Thus, there is need for a means of providing automatic relief for the condition of excess negativity in the pleural cavity.

In one of the applicant's pending U.S. Applications Ser. No. 256,152, a metered air pump is disclosed by which excess negative pressure can be relieved by pumping as many small units of air into the thoracotomy tube as necessary. In another of applicant's pending U.S. Applications Ser. No. 309,796, an automatically operated value connects the thoracotomy tube directly with the atmosphere whenever excess negativity occurs.

When excess negativity is relieved in the collection chamber and/or the thoracotomy tube, it is important that the pressure in the collection chamber and/or the thoracotomy tube be prevented from reaching atmospheric pressure. Should the pressure in the collection chamber and/or the thoracotomy tube reach atmospheric pressure, the collection chamber immediately ceases to drain fluids from the pleural cavity, a pneumothorax develops, and breathing of the patient can quickly become difficult. So long as the collection chamber and/or the thoracotomy tube are subatmospheric, a pneumothorax does not occur. However, if for some reason the imposed suction has been lost, for example, by inadvertent or temporary removal of the source of suction so that this portion of the drainage device is open to atmosphere, an inadvertent or intentional actuation of a relief valve directly open to the atmosphere may result in the collection chamber reaching atmospheric pressure as well.

SUMMARY OF THE PREFERRED EMBODIMENT OF THE INVENTION

The present invention provides a surgical underwater drainage device which overcomes the problems noted above with respect to prior art devices and provides an underwater drainage apparatus in which excess negativity can be safely relieved at all times. Furthermore, the apparatus provided assures that the excess negativity is relieved automatically and quickly while maintaining the appropriate desired negativity.

According to the present invention, there is provided a surgical underwater drainage apparatus having a collection chamber and an underwater seal chamber, and a suction control chamber. An outlet port adapted for connection to a source of suction is formed in a suction compartment located between the underwater seal chamber and the suction control chamber. Fluidly connecting the collection chamber and suction compartment is an excess negative pressure relief valve. This relief valve is resiliently biased closed and opens automatically when excess negativity occurs to connect the suction compartment and the collection chamber to relieve the excess negativity in the collection chamber. In order to prevent the collection chamber from reaching atmospheric pressure if the suction compartment is at atmospheric pressure, the relief valve closes automatically as well to prevent flow through the relief valve where the pressure in the collection chamber is more than a predetermined minimum below the pressure in the suction compartment.

In the preferred embodiment of the present invention, the relief valve includes an inlet tube with a distal end connected to the suction compartment and an outlet tube with a distal end connected to the collection chamber. The relief valve includes a body having a cylindrical bore provided with an inlet and an outlet connected, respectfully, to the proximal ends of the inlet tube and outlet tube. Located in the cylindrical bore is a piston whose face has a seal thereon which covers the inlet in the closed position of the valve. A spring is compressed on one side of the piston and urges the piston to the closed position. By chosing an appropriate spring, the refief valve prevents fluid flow from the suction compartment to the collection chamber where the pressure in the suction compartment does not exceed the pressure in the collection chamber by a predetermined minimum. Thus, the relief valve relieves excess negativity in the collection chamber until the pressure differential between the suction compartment and the collection chamber reaches the predetermined minimum. In this manner, the pressure in the collection chamber remains below that of the suction chamber; and even if the suction chamber is at atmospheric pressure, the pressure in the collection chamber is still less than atmospheric.

Additional features and advantages of the present invention will be apparent from a consideration of the following detailed description of the preferred embodiment of the invention in connection with the accompanying drawings.

BRIEF DESCRIPTIONS OF THE DRAWINGS

FIG. 1 is a cross-sectional plan front view of an underwater drainage device according to the present invention.

FIG. 2 is a partial rear plan view of the underwater drainage device depicted in FIG. 1 with the relief valve in cross section and showing the normal flow of air through the underwater drainage device.

DETAILED DESCRIPTION OF THE PREFERRED EMBODIMENT

With reference now to the drawings in which like numerals represent like elements throughout the several views, a presently preferred embodiment of a surgical underwater drainage device 10 is depicted in FIGS. 1 and 2. Underwater drainage device 10 has a housing 12 which contains a collection chamber 14, an underwater seal chamber 16, and a suction control chamber 18. Collection chamber 14 includes a inlet 20 through the top of housing 12 to which one end of a thoracotomy tube is connected. The other end of the thoracotomy tube is connected to the area of the patient to be drained. Underwater seal chamber 16 is provided with a small arm 22 and a large arm 24. Small arm 22 is completely separated from collection chamber 14 by a partition 26 except where a passage 28 is provided near the top of partition 26 as shown. Small arm 22 is also separated from large arm 24 by a partition 30 except for small passage 32 provided at the bottom of partition 30 in which a liquid seal is located. Located in small arm 22 is a one-way float valve 34 to prevent the passage of the liquid from small arm 22 through passage 28 into collection chamber 14.

Suction control chamber 18 also includes a small arm 40 and a large arm 42. Large arm 42 is separated from large arm 24 by a partition 44 except where passage 46 is provided at the top of partition 44. Small arm 40 is provided with a vent 48 in the top of housing 12 so that small arm 40 is open to the atmosphere. Small arm 40 is separated from large arm 42 by a partition 50 except for a passage 52 provided at the bottom of partition 50 in which a liquid seal is located.

Provided at the top of large arm 24 of underwater seal chamber 16 is an outlet 54 which is attachable to a suitable source of suction or negative pressure. The portions of both large arm 24 and large arm 42 above the liquid seals are directly subjected to the negative pressure provided through outlet 54 and these two arms form what will conveniently be referred to as a suction compartment 55. Adjacent outlet 54 is a positive pressure relief valve 56 having a seal 58 and a seat 60. Positive pressure relief valve 56 operates automatically to relieve any positive pressure created in suction compartment 55.

As shown in greater detail in FIG. 2, underwater drainage device 10 is provided with an automatically operating negative pressure relief valve 70. Relief valve 70 includes a valve body 72 with a cylindrical bore 74 therein and an end 76. Bore 74 is provided with a lateral inlet 78 and a lateral outlet 80. Located in a bore 74 is a piston 82 having a face 83 and a plurality of channels 84 along the longitudinal side thereof. An O-ring 86 is located in face 83. A spring 88 located between piston 82 and end 76 urges face 83 towards inlet 78 so that O-ring 86 normally surrounds inlet 78 and seals bore 74 from inlet 78. Thus, relief valve 70 is a "pop" type valve which only allows flow in one direction and which only opens when the fluid pressure differential between the pressure on face 83 of piston 82 and the pressure on the other side of face 83 is sufficient to overcome the force of spring 88. In the preferred embodiment, the pressure differential must exceed 5 cm. of water before relief valve 70 opens. Attached at one end of valve body 72 at inlet 78 is an inlet tube 90. Inlet tube 90 is attached at the other end to an aperture 92 provided in large arm 24 of underwater seal chamber 16. On the opposite side of valve body 72, an outlet tube 94 is attached at outlet 80. The other end of outlet tube 94 extends into collection chamber 14 and has a reduced outlet 96. As shown, restricted outlet 96 has a substantially reduced passage compared with the rest of outlet tube 94.

During normal operation, as described in applicant's prior patents referred to above, inlet 20 of collection chamber 14 is suitably connected to the area of the patient to be drained by a thoracotomy tube. Underwater seal chamber 16 and suction control chamber 18 are provided with suitable volumes of water to create the underwater seal and to control the pressure, respectively. Finally, outlet 54 is connected to a suitable source of suction or negative pressure. As passageway 46 connects large arm 42 of suction control chamber 18 and large arm 24 of underwater seal chamber 16, large arm 42 and large arm 24 (i.e. suction compartment 55) are maintained at the same pressure. This pressure is controlled by suction control chamber 18 and is, for example, minus 20 centimeters of water. Small arm 22 of underwater seal chamber 18 and collection chamber 14 are at the same pressure due to the provision of passage 28. Due to the small head of water provided in underwater seal chamber 16, the pressure in collection chamber 14 and small arm 22 is somewhat greater than the pressure maintained in suction compartment 55. For example, where the pressure in suction compartment 55 is minus 20 centimeters of water, the pressure in collection chamber 14 and small arm 22 is minus 18 centimeters of water. It should be appreciated that air is constantly bubbling through suction control chamber 18 from small arm 40 into large arm 42 so that the pressure in large arm 42 is maintained at minus 20 centimeters of water. In a similar manner, as fluids are collected in collection chamber 14, air bubbles through underwater seal chamber 16 from small arm 22 to large arm 24 whenever sufficient volumes of fluid are collected in collection chamber 14 to lower the pressure in collection chamber 14 below minus 18 centimeters of water.

When milking of the thoracotomy tube occurs, an increased negative pressure is produced in the pleural space, the thoracotomy tube, collection chamber 14 and small arm 22 of underwater seal 16. This increase of negative pressure can cause the pressure in collection chamber 14 to reach, for example, minus 50 centimeters of water. When this occurs, the water in underwater seal chamber 16 rises in small arm 22. If not for float valve 34, it would be possible during extreme excess negativity for the water in underwater seal chamber 16 to rise in small arm 22 and flow into collection chamber 14. While float valve 34 prevents this, float valve 34 does not prevent the water from rising in small arm 22 and thus maintaining the pressure differential between small arm 22 and large arm 24. This head of water produced in small arm 22 serves to indicate the fact that excess negativity exists in collection chamber 14.

As soon as the existence of excess negativity in collection chamber 14 occurs, negative pressure relief valve 70 operates automatically to begin relieving this excess negativity. This occurs automatically because the pressure on face 83 of piston 82 in relief valve 70 is the same as the pressure in suction compartment 55, in this example minus 20 cm. of water. As the pressure on the other side of face 83 is the same as that of collection chamber 14, in this example minus 50 cm. of water, the pressure differential is greater than 5 cm. of water and is sufficient to overcome the force of spring 88. Therefore, face 83 moves immediately away from inlet 78 and O-ring 86 moves out of sealing engagement around inlet 78. This movement allows air to flow from suction compartment 55, through negative pressure relief valve 70 (around piston 82 in channels 84) and into collection chamber 14 bypassing underwater seal chamber 16. As suction control chamber 18 still controls the pressure in suction compartment 55, the pressure in suction compartment 55 stays at minus 20 cm. of water as the air flows slowly through restricted outlet 96 and into collection chamber 14 and the dangerous excess negative pressure therein is relieved.

As soon as the pressure differential between suction compartment 55 and collection chamber 14 is at 5 cm. of water (i.e. 20 cm. of water and 25 cm. of water, respectively), relief valve 70 closes automatically because the pressure differential on face 83 is not sufficient to overcome the force of spring 88. Thus, the excess negative pressure in collection chamber 14 is relieved only to minus 25 cm. of water. Obviously, after most of the excess negativity is relieved and relief valve 70 closes, the water in underwater seal chamber 16 falls back near the bottom so that underwater seal chamber 16 is no longer bypassed and normal operation of drainage device 10 continues.

The small amount of excess negativity still in collection chamber 14 (i.e. 7 cm. of water more than the desired 18 cm. of water) does not do any harm to the operation of drainage device 10. As additional fluids enter collection chamber 14 from the thoracotomy tube, the pressure in collection chamber 14 soon returns to the equilibrium pressure of minus 18 cm. of water desired.

No matter what the pressure is in suction compartment 55, automatic actuation of negative pressure relief valve 70 in response to a pressure differential between collection chamber 14 and suction compartment 55 can only bring the pressure of collection chamber 14 to within 5 cm. of water of the pressure in suction compartment 55. As long as suction compartment 55 is maintained at a nagative pressure, there is no danger of collection chamber 14 reaching atmospheric pressure by the operation of relief valve 70. However, should the negative pressure in suction compartment 55 be lost through accidental disconnection of the suction source or a temporary disconnection and the pressure in suction chamber 55 reaches atmospheric pressure, automatic actuation of negative pressure relief valve 70 occurs and such actuation would allow collection chamber 14 to similarly reach atmospheric pressure with the possible disastrous results mentioned above if not for the safe design of relief valve 70. With relief valve 70, the lowest possible pressure which can be immediately achieved in chamber 14 is minus 5 cm. of water less than that of suction compartment 55. Thus, if suction compartment 55 is at atmospheric pressure when negative pressure relief valve 70 opens, the pressure in collection chamber 14 can only rise as high as minus 5 cm. of water before relief valve 70 automatically closes again. In such a situation, although the negative pressure in collection chamber 14 is then less than desired, the negative pressure is sufficient to prevent a pneumothorax while the dangerous atmospheric pressure condition of suction compartment 55 is noted and corrected.

Although prolonged periods of excess negativity in collection chamber 14 and in the pleural cavity of the patient are undesired, brief periods of excess negativity are often desired. For example, where a blockage to normal breathing occurs, the patient exerts a temporary excess negativity in the pleural cavity in an attempt to remove the blockage. Obviously, this excess negativity in the pleural cavity and in turn in collection chamber 14 is highly desired and it would be disadvantageous to relieve it. Due to the automatic operation to relief valve 70, any excess negativity (desired or not) causes relief valve 70 to open and to begin relieving this excess negativity. However, by use of restricted outlet 96, the flow of air from suction compartment 55 to collection chamber 14 is low enough so that excess negativity is only slowly relieved. Thus, when a condition occurs where desired excess negativity exists and is needed, the automatic operation of relief valve 70 does not substantially affect this needed excess negativity during the time period in which the excess negativity is needed and the condition is naturally relieved. However, where undesired excess negativity exists, the automatic operation of relief valve 70 to slowly bleed air from suction compartment 55 to collection chamber 14 is sufficient to relieve the excess negativity in collection chamber 14 before any harm to the patient can occur.

Should excess negativity again occur within collection chamber 14 after normal operation has again resumed, it is apparent that negative pressure relief valve 70 remains ready to relieve this excess negativity. It should be noted that relief valve 70 operates only to relieve the excess negativity in collection chamber 14, and can never totally destroy the desired negativity in collection chamber 14.

It should be appreciated that the force of spring 88 is chosen at a value to maintain a specific pressure differential between suction compartment 55 and collection chamber 14 and that the desired pressure differential can be altered by changing the force exerted by spring 88. In addition, other embodiments of negative pressure relief valve 70 are possible. The type and location of the air flow restriction means used with relief valve 70, and in the preferred embodiment restricted outlet 96, can also be varied. For example, a manually adjustable flow valve could be substituted for restricted outlet 96. It should also be noted that relief valve 70 only permits fluid flow in one direction so that there is no danger of liquids (or gases) being drawn into relief valve 70 and into suction compartment 55 whereby the operation of relief valve 70, underwater seal chamber 16, or suction control chamber 18 would be adversely effected.

In an alternative embodiment of the invention (not illustrated) the relief or pop valve 70 is omitted and inlet tube 90 and outlet tube 94 are interconnected by a tubular member so that a continuous passageway is provided between the large arm 24 of the water seal chamber and the collection chamber 14. However, by reason of the restricted passageway 96 excess negativity within the thoracotomy tube or the collection chamber will be relieved over a period of time. However, should the patient require excess negativity for breathing purposes the restricted passageway will permit the maintenance of such excess negativity for a short period of time.

Although the invention has been described relative to an exemplary embodiment thereof, it will be understood that variations and modifications can be effected in this embodiment without departing from the scope and spirit of the invention.

We claim:

1. A surgical underwater drainage device for collecting fluids from the body of a patient comprising:
    a collection chamber in which fluids from the patient are collected;
    an underwater seal chamber having a small arm and large arm, a first opening in said small arm in fluid communication with said collection chamber, a second opening in said large arm and a liquid seal disposed in said large arm and said small arm between said first opening and said second opening;
    an outlet port in communication with the second opening in said large arm in said underwater seal chamber;
    a separate automatically operated excess negative pressure relief valve means which fluidly connects said collection chamber and the large arm of said underwater seal chamber so as to bypass the liquid seal, said negative relief valve means opening automatically when the pressure in said large arm of said underwater seal chamber exceeds the pressure in said collection chamber by a predetermined amount to relieve the excess negativity in said collection chamber.

2. A drainage device as claimed in claim 1 and further including a suction control chamber having a manometer with one end open to atmosphere and with the other end in fluid communication with said second opening of said underwater seal chamber, said other end and said second opening forming a suction compartment; and wherein said outlet port is connected to a source of suction and is in fluid communication with said suction compartment.

3. A drainage device as claimed in claims 1 and 2 and further including a flow restriction means for allowing only a slow flow of air at a higher pressure through said relief valve to relieve the excess negative pressure in said collection chamber.

4. A drainage device as claimed in claim 3 wherein said flow restriction means is a reduced outlet portion of an outlet tube which connects said relief valve to said collection chamber.

5. A drainage device as claimed in claims 1 or 2 wherein said relief valve includes a valve body, an inlet and an outlet in said valve body, a piston slidably mounted in said body and having a face opposite said opening a seal means located on the face of said piston for sealing said inlet, and a resilient biasing means for urging said seal on the face of said piston into sealing engagement with said inlet whereby the force needed to overcome said resilient biasing means equal the force needed to open said relief valve.

6. A drainage device as claimed in claim 2 wherein the predetermined pressure differential between said suction compartment and said collection chamber below which said relief valve means does not open is 5 cm. of water.

* * * * *